United States Patent
Tsujita et al.

(10) Patent No.: US 8,617,075 B2
(45) Date of Patent: Dec. 31, 2013

(54) ULTRASONIC DIAGNOSTIC APPARATUS AND ULTRASONIC IMAGING METHOD

(75) Inventors: Takehiro Tsujita, Tokyo (JP); Tetsuya Hayashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1364 days.

(21) Appl. No.: 11/815,657

(22) PCT Filed: Feb. 9, 2006

(86) PCT No.: PCT/JP2006/302235
§ 371 (c)(1), (2), (4) Date: Aug. 7, 2007

(87) PCT Pub. No.: WO2006/085571
PCT Pub. Date: Aug. 17, 2006

(65) Prior Publication Data
US 2009/0209859 A1    Aug. 20, 2009

(30) Foreign Application Priority Data
Feb. 9, 2005 (JP) .................. 2005-032477

(51) Int. Cl.
*A61B 8/00* (2006.01)
*A61B 8/14* (2006.01)
*G06K 9/00* (2006.01)

(52) U.S. Cl.
USPC .................... 600/443; 600/458; 382/128

(58) Field of Classification Search
None
See application file for complete search history.

(56) References Cited

U.S. PATENT DOCUMENTS

| | | | |
|---|---|---|---|
| 5,608,849 A * | 3/1997 | King, Jr. | 345/419 |
| 5,682,895 A | 11/1997 | Ishiguro | |
| 5,810,008 A * | 9/1998 | Dekel et al. | 600/443 |
| 5,964,707 A * | 10/1999 | Fenster et al. | 600/443 |

(Continued)

FOREIGN PATENT DOCUMENTS

| | | |
|---|---|---|
| JP | 04-158855 | 6/1992 |
| JP | 07-047064 | 2/1995 |

(Continued)

OTHER PUBLICATIONS

Voluson 730Expert Basic User Manual, GE MEdical Systems 2004; chapter 11, pp. 48-51.*

*Primary Examiner* — Long V. Le
*Assistant Examiner* — Angela M Hoffa
(74) *Attorney, Agent, or Firm* — Antonelli, Terry, Stout & Kraus, LLP.

(57) ABSTRACT

An ultrasonic diagnostic apparatus is disclosed for imaging 3-dimensional images by irradiating ultrasonic waves to an object and reconstructing the 3-dimensional image. The ultrasonic diagnostic apparatus includes an ultrasonic probe for transmitting/receiving ultrasonic waves to/from an object to be examined, an ultrasonic image construction unit for constructing a 3-dimensional ultrasonic image based on the 3-dimensional ultrasonic image data from the ultrasonic signals received from the ultrasonic probe, and a display unit for displaying the 3-dimensional ultrasonic image. A position sensor is provided for detecting the position of the ultrasonic probe. A positional information analyzing unit stores the first position of the ultrasonic probe obtained from the position sensor and analyzes the positional relationship between the first position and the second position. The ultrasonic image construction unit converts the 3-dimensional ultrasonic image data obtained at the second position into a 3-dimensional ultrasonic image at the first position according to the positional relationship, thereby constructing the 3-dimensional ultrasonic image at the first position.

15 Claims, 7 Drawing Sheets

(56) References Cited

U.S. PATENT DOCUMENTS

| | | | |
|---|---|---|---|
| 6,167,296 A * | 12/2000 | Shahidi | 600/427 |
| 6,174,285 B1 * | 1/2001 | Clark | 600/443 |
| 6,203,497 B1 * | 3/2001 | Dekel et al. | 600/439 |
| 6,334,847 B1 * | 1/2002 | Fenster et al. | 600/443 |
| 6,336,899 B1 * | 1/2002 | Yamazaki | 600/443 |
| 6,351,573 B1 * | 2/2002 | Schneider | 382/294 |
| 6,544,178 B1 | 4/2003 | Grenon et al. | |
| 6,755,787 B2 * | 6/2004 | Hossack et al. | 600/447 |
| 7,270,634 B2 * | 9/2007 | Scampini et al. | 600/447 |
| 7,452,357 B2 * | 11/2008 | Vlegele et al. | 606/32 |
| 7,704,208 B2 * | 4/2010 | Thiele | 600/443 |
| 7,717,849 B2 * | 5/2010 | Mathew et al. | 600/437 |
| 2003/0097068 A1 * | 5/2003 | Hossack et al. | 600/443 |
| 2006/0020202 A1 * | 1/2006 | Mathew et al. | 600/437 |
| 2007/0032724 A1 * | 2/2007 | Thiele | 600/437 |
| 2009/0005679 A1 * | 1/2009 | Dala-Krishna | 600/437 |
| 2009/0156935 A1 * | 6/2009 | Frisa et al. | 600/447 |

FOREIGN PATENT DOCUMENTS

| | | |
|---|---|---|
| JP | 2000-107185 | 4/2000 |
| JP | 2001-079003 | 3/2001 |
| JP | 2004-016268 | 1/2004 |
| JP | 2004-121488 | 4/2004 |
| WO | WO 02/069807 | 9/2002 |

* cited by examiner

ULTRASONIC DIAGNOSTIC APPARATUS AND ULTRASONIC IMAGING METHOD

TECHNICAL FIELD

The present invention relates to an ultrasonic diagnostic apparatus and ultrasonic imaging method for scanning ultrasonic waves and displaying 3-dimensional ultrasonic images.

BACKGROUND ART

An ultrasonic diagnostic apparatus for imaging 3-dimensional images irradiates ultrasonic waves to an object to be examined via an ultrasonic probe, reconstructs 3-dimensional ultrasonic images based on a reflected echo signals generated from the object, and displays them on a display unit.

However, in the case of imaging internal organs of the object using the ultrasonic diagnostic apparatus, there are cases upon imaging a target region that obstacles such as a placenta or fat exist between the ultrasonic probe and the target region.

Given this factor, in Patent Document 1, a 3-dimensional ultrasonic image viewing from an arbitrarily set viewpoint direction is constructed and displayed, by arbitrarily changing the viewpoint in 3-dimensional ultrasonic image data obtained via the ultrasonic probe. However, when there is an obstacle between the ultrasonic probe and the target region, the ultrasonic image data obtained by the scanning of the ultrasonic probe include the obstacle. Even with the usage of the method in Patent Document 1, the image acquired by constructing the 3-dimensional ultrasonic image by setting the ultrasonic probe thereto would include the obstacle. Therefore, even when the viewpoint position for displaying the 3-dimensional ultrasonic image is changed, since the 3-dimensional ultrasonic image data obtained from the ultrasonic probe would not be changed, the influence caused by the obstacle on the 3-dimensional ultrasonic image still remains the same.

Patent Document 1: JP-A-2001-79003

The objective of the present invention, upon imaging internal organs of the object using the ultrasonic diagnostic apparatus, is to display 3-dimensional ultrasonic images by stabilizing the display figure.

DISCLOSURE OF THE INVENTION

In order to achieve the objective of the present invention, an ultrasonic diagnostic apparatus comprises:
  an ultrasonic probe for transmitting/receiving ultrasonic waves to/from an object to be examined;
  an ultrasonic image construction unit for constructing a 3-dimensional image from 3-dimensional ultrasonic image data based on the ultrasonic signals received from the ultrasonic probe; and
  a display unit for displaying the 3-dimensional ultrasonic image,
  characterized in comprising:
  a positional sensor for detecting the position of the ultrasonic probe; and
  a positional information analyzing unit for storing the first position of the ultrasonic probe obtained by the position sensor, and analyzing the positional relationship between the first position and the second position,
  wherein the ultrasonic image construction unit constructs the 3-dimensional ultrasonic image in the first position by converting the 3-dimensional ultrasonic image data obtained in the second position into the data to be the 3-dimensional ultrasonic image in the first position based on the positional relationship.

The positional information analyzing unit analyses the positional relationship based on the positional variation between the first position and the second position of the ultrasonic probe and the variation of the 3-dimensional rotation angle thereof, and computes adjustment parameter for converting the 3-dimensional ultrasonic image data, from conversion information indicating the first position of the ultrasonic probe and the conversion information indicating the second position of the ultrasonic probe. Then the image construction unit converts the 3-dimensional ultrasonic image data based on the positional relationship or the adjustment parameter.

Also, an ultrasonic imaging method of the present invention includes:
  a step of setting an ultrasonic probe at the first position and storing the first position thereof;
  a step of setting the ultrasonic probe at a second position and acquiring 3-dimensional ultrasonic image data;
  a step of converting the 3-dimensional ultrasonic image data into the 3-dimensional ultrasonic image data in the first position, based on positional relationship between the first position and the second position; and
  a step of constructing the converted 3-dimensional ultrasonic image and displaying it.

BRIEF DESCRIPTION OF THE DIAGRAMS

BEST MODE TO CARRY OUT THE INVENTION

The first embodiment of the ultrasonic diagnostic apparatus to which the present invention is applied will be described referring to the diagrams. This embodiment is an example for displaying the target region viewing from a certain direction without depending on the position of the ultrasonic probe, using a position sensor connected to an ultrasonic probe.

Figure 1:
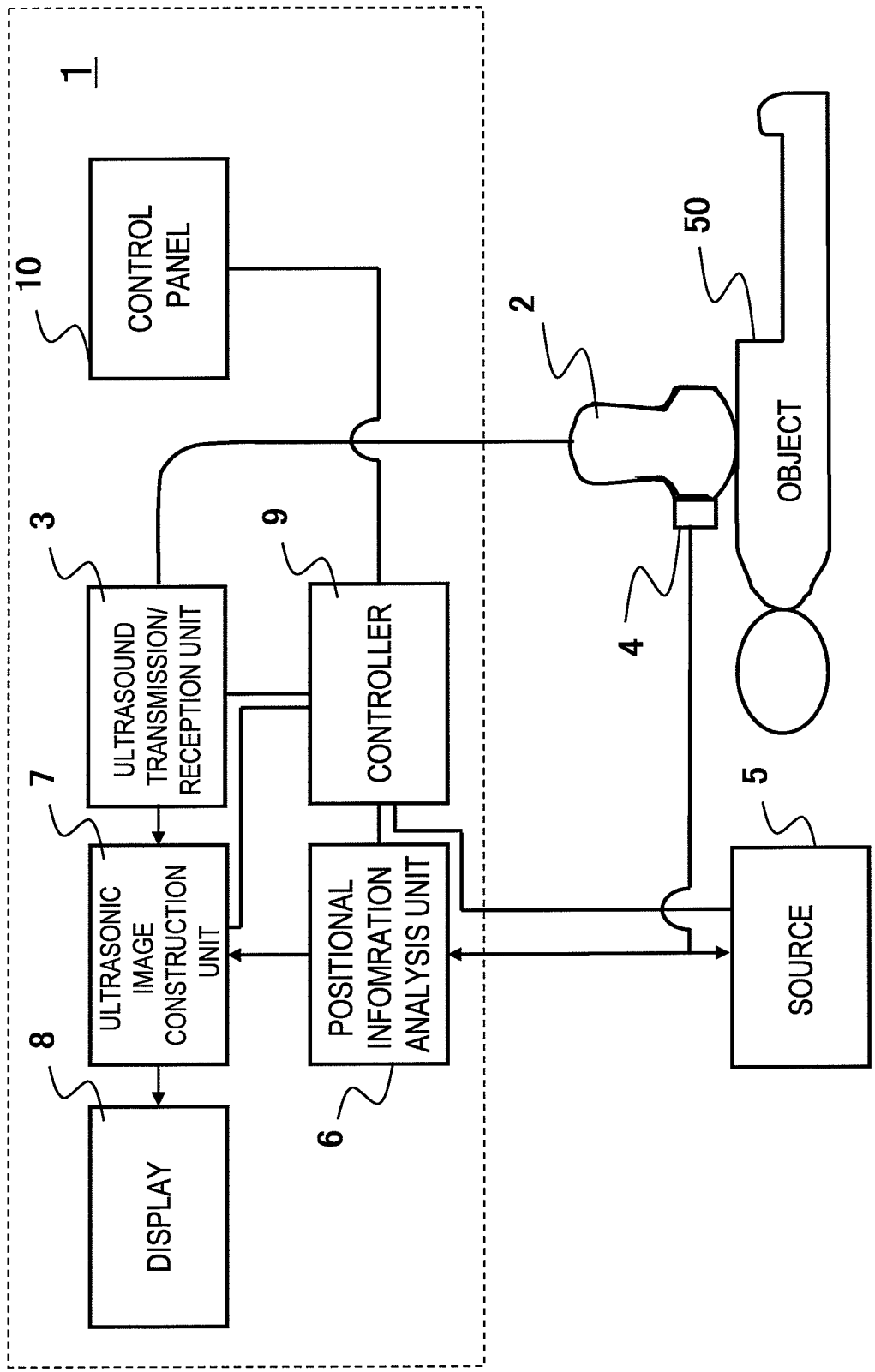
FIG. 1 is a block diagram showing the ultrasonic diagnostic apparatus of the present invention.

FIG. 1 is a block diagram showing the ultrasonic diagnostic apparatus related to the present embodiment. Ultrasonic diagnostic apparatus 1 shown in FIG. 1 comprises:
  ultrasonic probe 2 in which the transducer elements for transmitting/receiving ultrasonic waves are arranged;
  ultrasound transmitting/receiving unit 3 for transmitting ultrasound signals to object 50 via ultrasonic probe 2 and performing process such as phasing addition and Log compression with respect to the received ultrasound signals;
  position sensor (terminal) 4 being attached to ultrasonic probe 2;
  source 5 for detecting the position of position sensor 4 using magnetic signals and the like;

positional information analyzing unit 6 for analyzing positional information of position sensor 4 from source 5, and computing adjustment parameter for adjusting 3-dimensional ultrasonic image data;

ultrasonic image construction unit 7 for performing process such as filtering and scan conversion with respect to the 3-dimensional ultrasonic image data from ultrasound transmitting/receiving unit 3, and reconstructing a 3-dimensional ultrasonic image using the adjustment parameter from positional information analyzing unit 6;

display 8 for displaying the images;

controller 9 being connected to all modules to control them; and control panel 10 for giving commands to controller 9.

Figure 2:
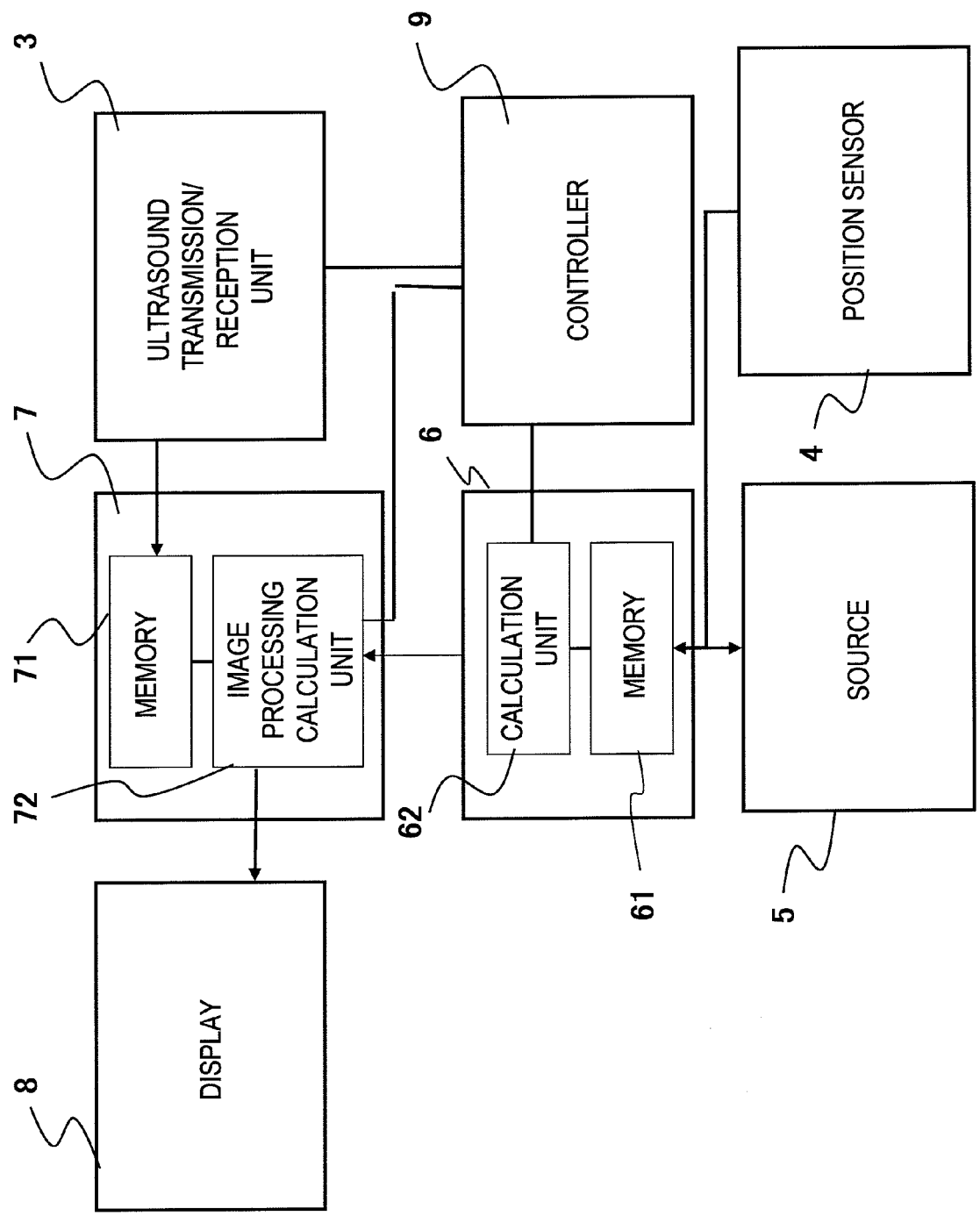
FIG. 2 is a diagram showing the details of the block diagram of the ultrasonic diagnostic apparatus related to the present invention.

Also, as shown in FIG. 2, positional information analyzing unit 6 is provided with memory 61 for storing the position of ultrasonic probe 2 and calculation unit 62 for computing adjustment parameter and the like from positional information stored in memory 61, and ultrasonic image construction unit 7 is provided with memory 71 for storing 2-dimensional or 3-dimensional ultrasonic images and image processing calculation unit 72 for adjusting 3-dimensional ultrasonic image data using adjustment parameter and the like and constructing 3-dimensional ultrasonic images.

In ultrasonic probe 2, transducer elements are arranged in major axis direction for 1~m channels, and also in minor direction for 1~k channels being cut into k-numbers.

Ultrasonic probe 2 is configured such that focusing of transmission or reception can be performed in major and minor directions by imparting varying delay time to the respective transducer elements (1~k channels). Also, ultrasonic probe 2 is configured to be capable of performing weighting on transmission waves by varying amplitude of ultrasound transmission signals given to the respective transducer elements in minor direction, and performing weighting on reception waves by varying amplification degree or attenuance of ultrasound receiving signals from the respective transducer elements in minor direction. Furthermore, it is configured capable of controlling the aperture of the transducer by turning on/off the respective transducer elements in minor direction. For ultrasonic probe 2, a mechanical ultrasonic probe can be used for scanning ultrasonic waves and obtaining 3-dimensional ultrasonic images while reciprocating the transducer mechanically in minor direction.

In the case of obtaining the 3-dimensional ultrasonic image using this type of ultrasonic probe 2, memory 71 in ultrasonic image construction unit 7 first scans ultrasonic waves and stores 2-dimensional ultrasonic image data. Then ultrasonic image construction unit 7 reads out 2-dimensional ultrasonic image data one frame at a time in order, and the respective frames are added up by an accumulator in ultrasound image construction unit 7, and the 3-dimensional ultrasonic image is thus constructed. 2-dimensional ultrasonic image data and the positional data of ultrasonic probe 2 are linked to each other at this time.

Position sensor 4 is attached to ultrasonic probe 2. Position sensor 4 is configured having, for example, a magnetic sensor for detecting magnetic signals generated from source 5 mounted in a bed and the like. 3-dimensional position and tilt of ultrasonic probe 2 in source coordinate system S are detected by position sensor 4. Source coordination system S is a 3-dimensional orthogonal coordinate system having source 5 as origin "So", wherein X-axis is set as minor direction of a bed on which an object is laid, Y-axis as major direction of the bed, and Z-axis as vertical direction. Source coordination system S does not have to be limited to a 3-dimensional orthogonal coordinate system, but needs to be the one capable of identifying the position of ultrasonic probe 2. Also, position sensor 4 does not have to be limited to a magnetic kind, and may be, for example, an optical kind.

Figure 3:
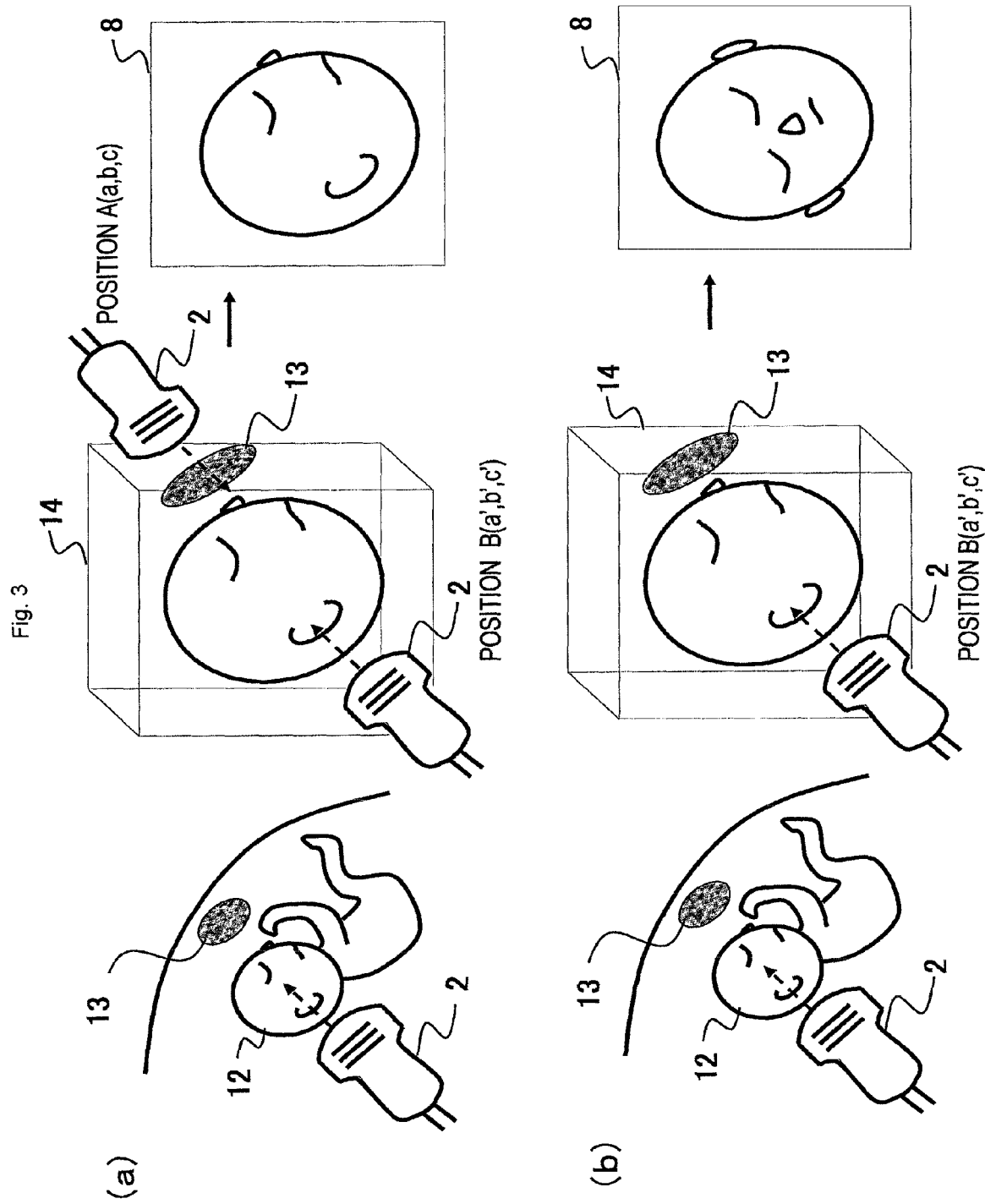
FIG. 3 is a schematic diagram of the display process showing the fourth embodiment of the present invention.

FIG. 3 is a schematic diagram showing the image processing of the present embodiment. As shown in FIG. 3(*a*), while position A(a,b,c) is a position for imaging a frontal view of target region 12, obstacle 13 is displayed on 3-dimensional ultrasonic image in position A(a,b,c). Given this factor, ultrasonic probe 2 is set at position B(a',b',c'), and scans ultrasonic waves with respect to target region 12. Since there is no obstacle 13 between ultrasonic probe 2 and target region 12, the 3-dimensional ultrasonic image acquired by scanning would not include obstacle 13. When reconstruction of the image is thus executed by setting ultrasonic probe 2 at position B(a',b',c'), a lateral view of target region 12 is displayed.

With that, memory 61 in positional information analyzing unit 6 stores the position of ultrasonic probe 2 acquired by position sensor 4, and calculation unit 62 in positional information analyzing unit 6 analyzes the positional relationship between position A(a,b,c) and position B(a',b',c') stored in memory 61. Image processor 72 in ultrasonic image construction unit 7 constructs 3-dimensional ultrasonic images by converting 3-dimensional ultrasonic image data acquired from position B(a',b',c') into the data of position A(a,b,c) based on the positional relationship. At this time, position B(a',b',c') may be stored in memory 61.

In concrete terms, calculation unit 62 in positional information analyzing unit 6 sets position A(a,b,c) of ultrasonic probe 2 as the conversion matrix to be display position of the 3-dimensional ultrasonic image. Next, calculation unit 62 sets the conversion matrix of position B(a',b',c') after the direction of ultrasonic probe 2 has been changed. Then, the variation of 3-dimensional rotation angle (adjustment parameter) is computed from the conversion matrix of position A(a,b,c) and position B(a',b',c'). Image processing calculation unit 72 performs coordinate conversion of the 3-dimensional ultrasonic image based on the adjustment parameter, and changes the display direction of the 3-dimensional ultrasonic image.

Here, calculation method of adjustment parameter in positional information analyzing unit 6 will be described. On the basis of the reference axis of position sensor 4, conversion matrix S indicating the position and direction of ultrasonic probe 2 at position A(a,b,c) is set as formula (1), and conversion matrix D indicating the position and direction of ultrasonic probe 2 at position B(a',b',c') is set as formula (2). This conversion matrix is stored in memory 61. Then, when rotation matrix V with respect to 3-dimensional ultrasonic image data 14 in position A(a,b,c) which is arbitrarily determined regarding ultrasonic probe 2 is expressed as formula (3), calculation unit 62 sets conversion matrix X from position A(a,b,c) to position B(a',b',c') as formula (6) by formula (5). Therefore, relationship between parameter M, conversion matrix X and rotation matrix V is expressed as formula (7).

For the sake of simplification, in the case of carrying out only display angle compensation from rotational components, it is set as (ds1,ds2,ds3)=(0,0,0) in formula (1), =(dv1, dv2,dv3)=(0,0,0) in formula (2), and (dd1,dd2,dd3)=(0,0,0) in formula (3).

Therefore, adjustment parameter M can be calculated by formula (8) in calculation unit 62. In other words, 3-dimensional ultrasonic image data 14 acquired at position B(a',b',c') of ultrasonic probe 2 is rotated having the center of the 3-dimensional ultrasonic image as an origin, using the coordinate conversion represented by adjustment parameter M. Image processing calculation unit 72 can obtain the 3-dimensional ultrasonic image from direction of position A(a,b,c) by reconstructing the 3-dimensional ultrasonic image thus being rotated.

[Formula 1]

$$S = \begin{pmatrix} a_{s1} & b_{s1} & c_{s1} & d_{s1} \\ a_{s2} & b_{s2} & c_{s2} & d_{s2} \\ a_{s3} & b_{s3} & c_{s3} & d_{s3} \\ 0 & 0 & 0 & 1 \end{pmatrix} \quad (1)$$

[Formula 2]

$$D = \begin{pmatrix} a_{d1} & b_{d1} & c_{d1} & d_{d1} \\ a_{d2} & b_{d2} & c_{d2} & d_{d2} \\ a_{d3} & b_{d3} & c_{d3} & d_{d3} \\ 0 & 0 & 0 & 1 \end{pmatrix} \quad (2)$$

[Formula 3]

$$V = \begin{pmatrix} a_{v1} & b_{v1} & c_{v1} & d_{v1} \\ a_{v2} & b_{v2} & c_{v2} & d_{v2} \\ a_{v3} & b_{v3} & c_{v3} & d_{v3} \\ 0 & 0 & 0 & 1 \end{pmatrix} \quad (3)$$

[Formula 4]

$$M = \begin{pmatrix} a_{m1} & b_{m1} & c_{m1} & d_{m1} \\ a_{m2} & b_{m2} & c_{m2} & d_{m2} \\ a_{m3} & b_{m3} & c_{m3} & d_{m3} \\ 0 & 0 & 0 & 1 \end{pmatrix} \quad (4)$$

[Formula 5]

$$D = S \cdot X \quad (5)$$

[Formula 6]

$$X = D \cdot S^{-1} \quad (6)$$

[Formula 7]

$$M = X^{-1} \cdot V \quad (7)$$

[Formula 8]

$$M = D^{-1} \cdot S \cdot V \quad (8)$$

Figure 4:
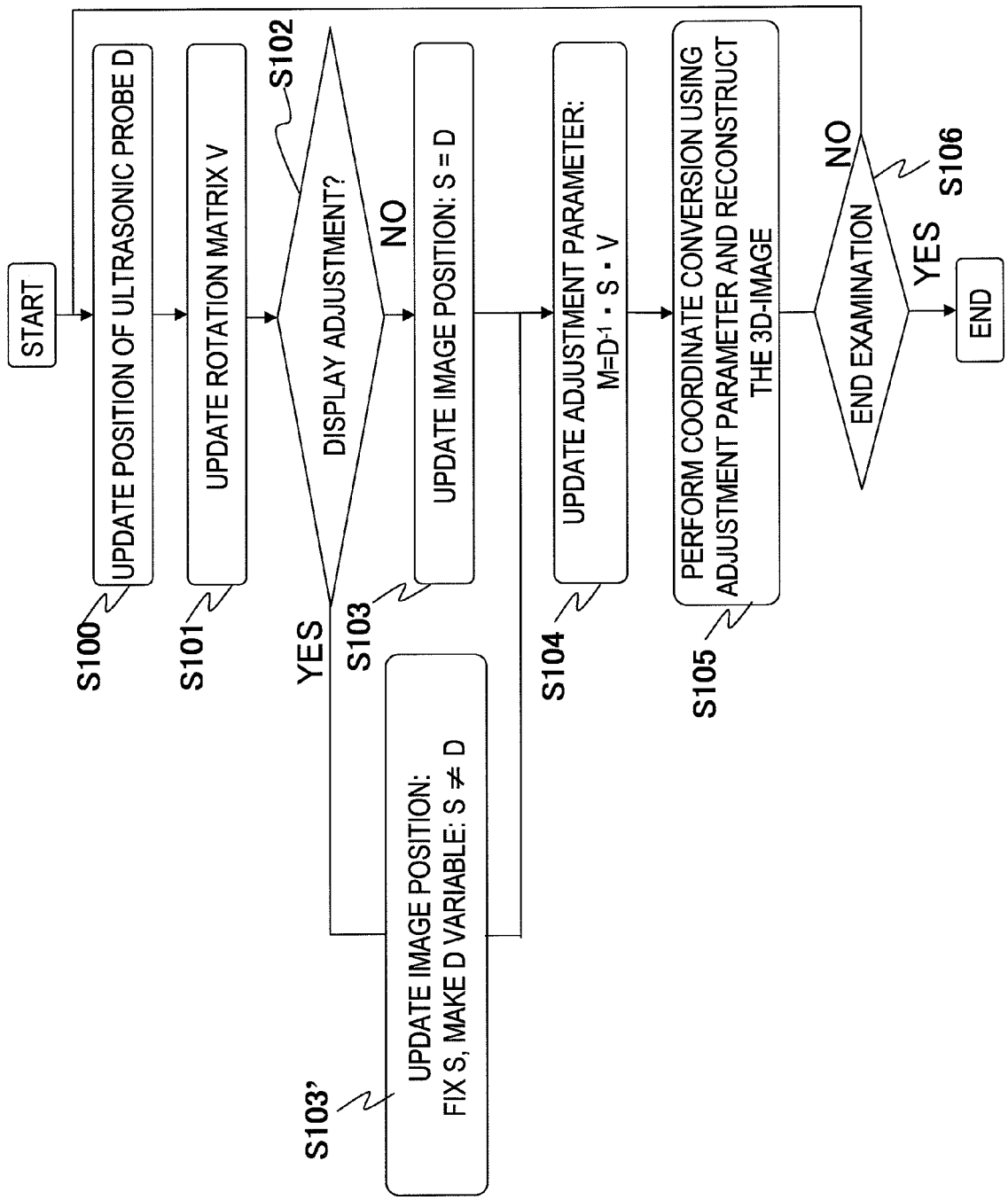
FIG. 4 is a diagram showing a flow chart of the display process related to the present invention.

FIG. 4 is a flow chart showing a procedure for computing the position adjustment parameter. After ultrasound examination is started, calculation unit 62 in positional information analyzing unit 6 updates conversion matrix D indicating the current position of ultrasonic probe 2 (S100) and updates rotation matrix V being inputted from control panel 10 (S101). Then the 3-dimensional ultrasonic image acquired in position B(a',b',c') being suited to position A(a,b,c) is adjusted, that is, when the display adjustment function is on (S102), conversion matrix S indicating the position of ultrasonic probe 2 before the movement (position A(a,b,c)) is fixed, and conversion matrix D is variably set (S103'). In other words, it is expressed as: conversion matrix S≠conversion matrix D. The 3-dimensional ultrasonic image is then constructed using the coordinate conversion by adjustment parameter computed by (S104) in image processing calculation unit 72 in ultrasonic image construction unit 7, and displayed on display 8. If "end the examination" is not selected in controller 9 the procedure will be executed again from (S100) and if "end the examination" is selected the process is terminated (S106).

In addition, when the present invention is not applied, adjustment for making the display position to be suited to position A(a,b,c) will not be executed on the 3-dimensional ultrasonic image. In other words, when the display adjustment function is not on (S102), calculation unit 62 in positional information analyzing unit 6 substitutes conversion matrix S indicating the position of ultrasonic probe 2 before movement (position A(a,b,c)) with conversion matrix D (S103), and computes adjustment parameter M using the above formula (S104). Since conversion matrix S=conversion matrix D at this time, adjustment parameter M becomes the conversion matrix which executes only rotation matrix V inputted from control panel 10.

When the display adjustment function is turned on through control panel 10 (S102), conversion matrix S indicating the position of ultrasonic probe 2 before movement (position A(a,b,c)) does not get updated, thus adjustment parameter M computed in (S104) becomes the conversion matrix which performs rotation matrix V being inputted by control panel 10, and the movement from conversion matrix D representing the current position of ultrasonic probe 2 to conversion matrix S indicating the position of ultrasonic probe 2 before movement (position A(a,b,c)). In other words, the previously mentioned adjustment parameter M reconstructs the 3-dimensional ultrasonic image with respect to the 3-dimensional ultrasonic image data scanned in the current position A(a,b,c) of ultrasonic probe 2 converted from the 3-dimensional ultrasonic image data scanned in position B(a',b',c') of ultrasonic probe 2, from the position of the same display direction of the case that the coordinate conversion by rotation matrix V being inputted from control panel is performed. While conversion matrix D indicating the current position B(a',b',c') of ultrasonic probe 2 is updated with respect to each scanning, conversion matrix S indicating position A(a,b,c) of ultrasonic probe 2 before the movement does not get updated while the display adjustment is on, whereby making it possible to consistently maintaining the display condition of the case being observed in position A(a,b,c) of ultrasonic probe 2 before movement regardless of the current position B(a',b',c') of ultrasonic probe 2.

In this way, calculation unit 62 in positional information analyzing unit 6 rotates 3-dimensional ultrasonic image data 14 by the positional information in position A(a,b,c) and position B(a',b',c') of ultrasonic probe 2, and computes the adjustment parameter for acquiring the same image as the 3-dimensional ultrasonic image in position A(a,b,c). And image processing calculation unit 72 in ultrasonic image construction unit 7 automatically acquires the 3-dimensional ultrasonic image by reconstructing 3-dimensional ultrasonic image data 14 using the above-mentioned adjustment parameter.

Here, another embodiment for performing rotation conversion on 3-dimensional ultrasonic image data 14 will be described. First, memory 61 in positional information analyzing unit 6 displays the frontal image of target region 12, and stores position A(a,b,c) as the display position. Then memory 61 stores position B(a',b',c') wherein obstacle 13 is not included in the ultrasonic image. These positional information are transmitted to calculation unit 62 in positional information analyzing unit 6, and calculation unit 62 computes positional variation of position B(a',b',c') with respect to position A(a,b,c) and displacement magnitude of the 3-dimensional rotation angle thereof. Then image processing calculation unit 72 rotates the 3-dimensional ultrasonic image only for the varied portion of the position and angle of ultrasonic probe 2, and displays the 3-dimensional ultrasonic image so that position A(a,b,c) becomes the display position.

In concrete terms, the normal vector of the planar image displayed in position A(a,b,c) and the normal vector of the planar image displayed in position B(a',b',c') represent, when they intersect on the 3-dimensional ultrasonic image data, variation of the 3-dimensional rotation angle centering on the intersection. The above-mentioned variation is decomposed into the rotation around X-axis, rotation around Y-axis and rotation around Z-axis, and the respective rotations are expressed by the following rotation matrix:

First the rotation of angle θ1 around X-axis is expressed as:

[Formula 9]

$$\begin{pmatrix} X \\ Y \\ Z \end{pmatrix} = \begin{pmatrix} 1 & 0 & 0 \\ 0 & \cos\theta_1 & \sin\theta_1 \\ 0 & -\sin\theta_1 & \cos\theta_1 \end{pmatrix} \begin{pmatrix} x \\ y \\ z \end{pmatrix}, \quad (9)$$

the rotation of angle θ2 around Y-axis is expressed as:

[Formula 10]

$$\begin{pmatrix} X \\ Y \\ Z \end{pmatrix} = \begin{pmatrix} \cos\theta_2 & 0 & -\sin\theta_2 \\ 0 & 1 & 0 \\ \sin\theta_2 & 0 & \cos\theta_2 \end{pmatrix} \begin{pmatrix} x \\ y \\ z \end{pmatrix}, \quad (10)$$

and the rotation of angle 3 around Z-axis is expressed as:

$$\begin{pmatrix} X \\ Y \\ Z \end{pmatrix} = \begin{pmatrix} \cos\theta_3 & \sin\theta_3 & 0 \\ -\sin\theta_3 & \cos\theta_3 & 0 \\ 0 & 0 & 1 \end{pmatrix} \begin{pmatrix} x \\ y \\ z \end{pmatrix}. \quad (11)$$

Therefore, rotation conversion is performed on 3-dimensional ultrasonic image data 14 from position B(a',b',c') to position A(a,b,c), by applying unit vector (1,0,0) of X-direction, unit vector (0,1,0) of Y-direction and unit vector (0,0,1) of Z-direction to 3-dimensional ultrasonic image data 14 of position B(a',b',c') in the respective X,Y and Z directions thereto. By reconstructing the 3-dimensional ultrasonic image based on the 3-dimensional ultrasonic image data 14 thus rotated, it is possible to display the 3-dimensional ultrasonic image in the display direction from position A(a,b,c).

In this way, in accordance with the first embodiment, it is possible to display the 3-dimensional ultrasonic image in display direction from position A(a,b,c) using image processing calculation unit 72 by converting the 3-dimensional ultrasonic image data acquired from position B(a',b',c'),based on the positional relationship between position A(a,b,c) and position B(a',b',c') of ultrasonic probe 2. In other words, once a certain position of ultrasonic probe 2 is specified, the 3-dimensional ultrasonic image viewing from the specified position can be displayed even when ultrasonic probe 2 is moved.

Also, even when changes occurs on the 3-dimensional ultrasonic image data acquired from position B(a',b',c') due to factors such as the hand holding ultrasonic probe 2 being jiggled, since position A(a,b,c) is fixed, it is possible to display the 3-dimensional ultrasonic image stably from position A(a,b,c).

Figure 5:
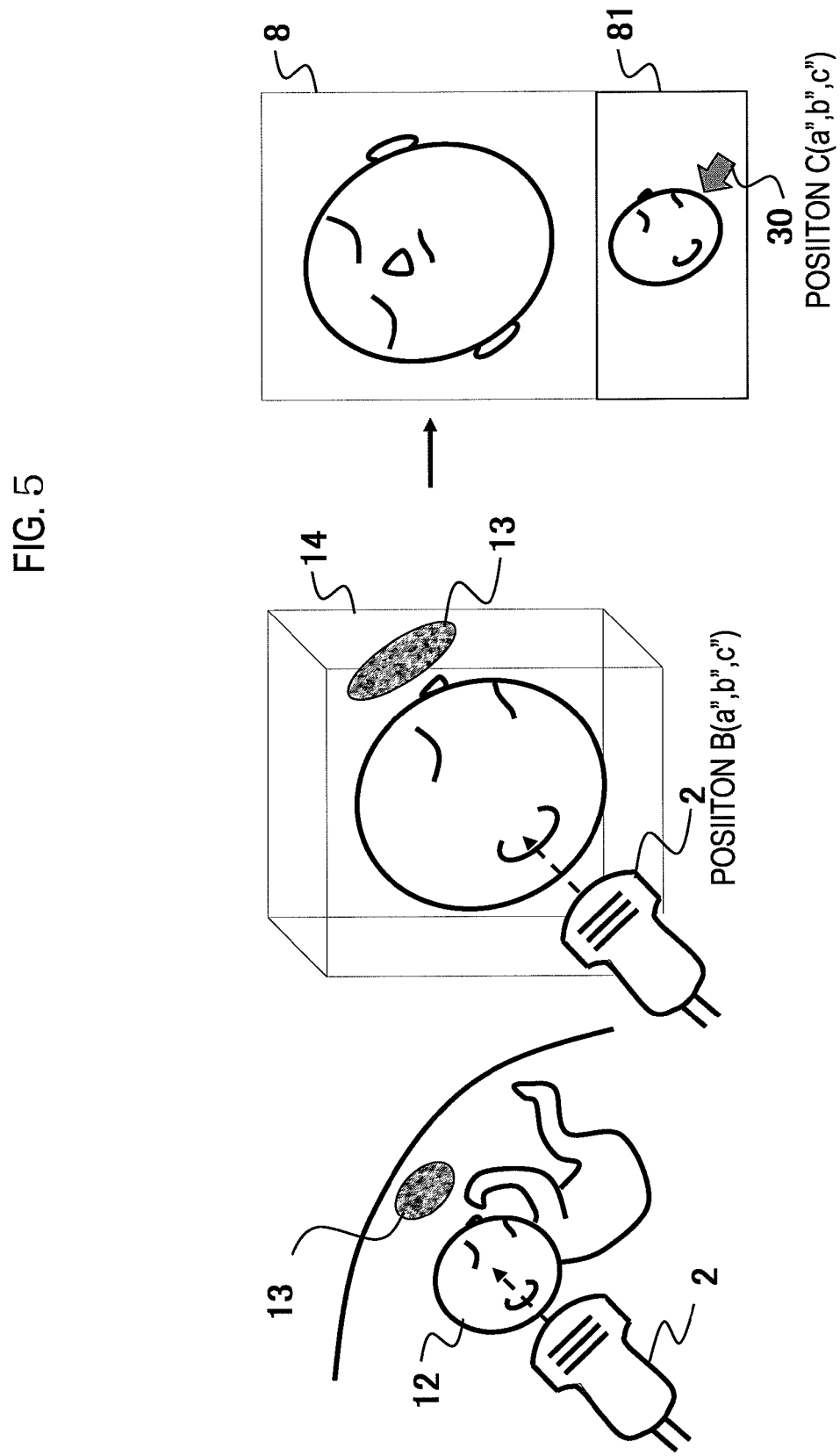
FIG. 5 is a diagram showing the second embodiment of the present invention.

Next, the second embodiment will be illustrated in FIG. 5. The difference from embodiment 1 is that direction indicator mark 30 to indicate the display direction is displayed 3-dimensionally, and target region 12 corresponding to the direction indicator mark 30 is displayed. On display 8, a 3-dimensional ultrasonic image and subsidiary image 81 are displayed. On subsidiary image 81, a 3-dimensional ultrasonic image viewing from position B(a',b',c') to which ultrasonic probe 2 is applied, and direction indicator mark 30 for indicating the display direction are displayed. The direction indicator mark 30 is 3-dimensionally moved around target region 12 using control-panel 10. The direction indicator mark 30 is directed toward the center point of target region 12.

Here, the position of direction indicator mark 30 is set as, position C(a'',b'',c'') display position. Direction indicator mark 30 in FIG. 5 indicates the position for imaging target region 12 from the underside direction. Calculation unit 62 in positional information analyzing unit 6 computes adjustment parameter of position B(a',b',c') corresponding to position C(a'',b'',c'') using the same method as the above embodiment 1, and computes variation of the positions and displacement magnitude of the 3-dimensional rotation angle. Then image processing calculation unit 72 constructs the rotated 3-dimensional ultrasonic image, and displays the 3-dimensional ultrasonic image viewed from position C(a'',b'',c'') that is from direction indicator mark 30 on display 8. Accordingly, this embodiment enables the observation of the 3-dimensional ultrasonic image from the set direction of direction indicator mark 30.

Also, direction indicator mark 30 is moved using control-panel 10 while ultrasonic probe 2 is being fixed on object 50. Along with the movement of direction indicator mark 30, calculation 62 in positional information analyzing unit 6 computes the variation of the position and displacement magnitude of the 3-dimensional rotation angle in real time. Then by constructing the rotated 3-dimensional ultrasonic image in real time based on variation of the position and displacement magnitude of the 3-dimensional rotation angle, it is possible to stably display the 3-dimensional ultrasonic image directed from direction indicator mark 30 on display 8. In accordance with the second embodiment, adjustment of the 3-dimensional ultrasonic image viewed from direction indicator mark 30 can be executed.

Figure 6:
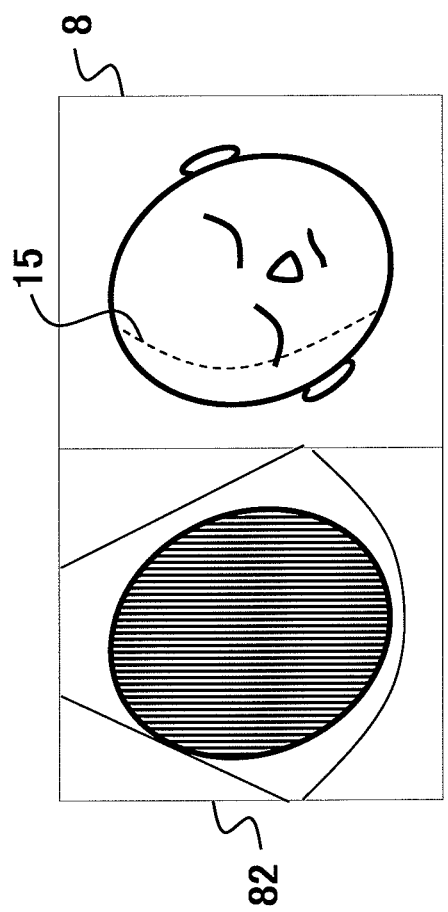
FIG. 6 is a diagram showing the third embodiment of the present invention.

Next, the third embodiment will be illustrated in FIG. 6. The difference from the first and the second embodiments is that a 3-dimensional ultrasonic image and a B-mode image are displayed at the same time. The B-mode image here is the one imaged from the scanning direction of ultrasonic probe 2.

Dotted line 15 is a sliced plane of a B-mode image corresponding to the 3-dimensional ultrasonic image displayed on display 8. Dotted line 15 can be moved by control panel 10, positional information of dotted line 15 is acknowledged by positional information analyzing unit 6, and image processing calculation unit 72 selects the B-mode image of the cross section corresponding to dotted line 15 from 3-dimensional ultrasonic image data 14 and displays it on display 8. In this way, the outer circumferential surface and the inside of object 50 can be displayed at the same time, and when an operator desires to observe a B-mode image, the change to do so can be made arbitrarily. Consequently, in accordance with embodiment 3, it is possible to display a 2-dimensional ultrasonic image from the display direction of position A(a,b,c), by converting the 3-dimensional ultrasonic image data obtained from position B(a',b',c') based on the positional relationship between position A(a,b,c) and position B(a',b',c') of ultrasonic probe 2. In other words, once a certain position of ultrasonic probe 2 is specified, the 2-dimensional ultrasonic image viewed from the position thereof can be displayed even while ultrasonic probe 2 is being moved.

While initial setting of dotted line 15 is set as the scanned surface of ultrasonic probe 2, it may be displayed along with the above-mentioned position A(a,b,c), B(a',b',c'), C(a",b",c") or direction indicator mark 30.

Next, the fourth embodiment will be described using FIG. 3. The difference from embodiments 1~3 is the point that more than two 3-dimensional ultrasonic images are synthesized.

Regarding 3-dimensional ultrasonic image data 14 obtained by scanning ultrasonic waves from position B(a',b',c'), while 3-dimensional ultrasonic image data on ultrasonic probe 2 side is sufficient, 3-dimensional ultrasonic image data on the backside which is symmetric with respect to the point of position B(a',b',c') is insufficient. In FIG. 3, while the 3-dimensional ultrasonic image data on the right ear side to which ultrasonic probe 2 is applied is sufficient, the 3-dimensional ultrasonic image data on the left ear side of target region 12 is insufficient. Given this factor, 3-dimensional ultrasonic image data 14 of the side that the data is insufficient is stored in memory 17 in advance, and image processing calculation unit 72 synthesizes the 3-dimensional ultrasonic image data stored in memory 71 and the 3-dimensional ultrasonic image obtained in real time.

The above-mentioned synthesizing function will be described in concrete terms. Image processing calculation unit 72 in ultrasonic image construction unit 7 has a function for synthesizing more than two 3-dimensional ultrasonic images. First, a 3-dimensional ultrasonic image is obtained by scanning ultrasonic waves to object 50, and stored in memory 71. At this time, a reference point of the 3-dimensional ultrasonic image is set using the positional information of position sensor 4, and the reference point is stored in memory 71. Then the position of ultrasonic probe 2 is changed, ultrasonic waves are scanned to object 50, and the 3-dimensional ultrasonic image is thus obtained in real time. Next, image processing calculation unit 72 matches in real time the reference point of the 3-dimensional ultrasonic image stored in memory 71 and the reference point of the 3-dimensional ultrasonic image, and superimposes the stored 3-dimensional ultrasonic image and the real time 3-dimensional ultrasonic image. Upon superimposing more than two 3-dimensional ultrasonic images, the 3-dimensional ultrasonic image having higher luminance is preferentially displayed. In addition, the number of 3-dimensional ultrasonic images to be superimposed may be more than 3.

In this way, memory 71 stores in advance the 3-dimensional ultrasonic image data that is insufficient, and image processing calculation unit 72 adjusts the real time 3-dimensional ultrasonic image using the previously mentioned 3-dimensional ultrasonic image data. Consequently, in accordance with the fourth embodiment, it is possible to display 3-dimensional ultrasonic images having uniform luminance from any angles.

Next, the fifth embodiment will be described using FIG. 7. The difference of this embodiment from embodiments 1~4 is the setting of the pre-cut line for partially deleting the 3-dimensional ultrasonic image data.

Figure 7:
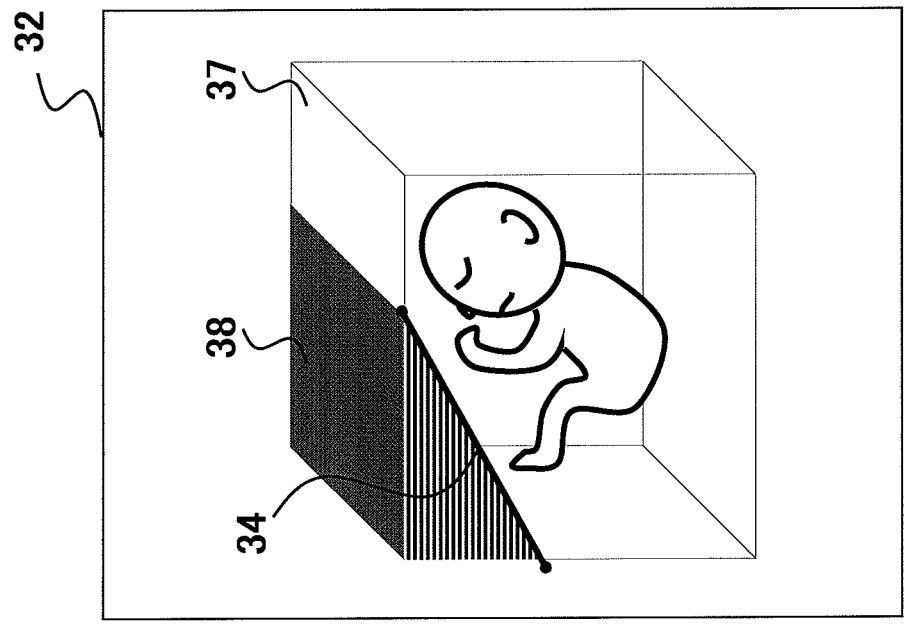
FIG. 7 is a diagram showing the fifth embodiment of the present invention.
Figure 7:
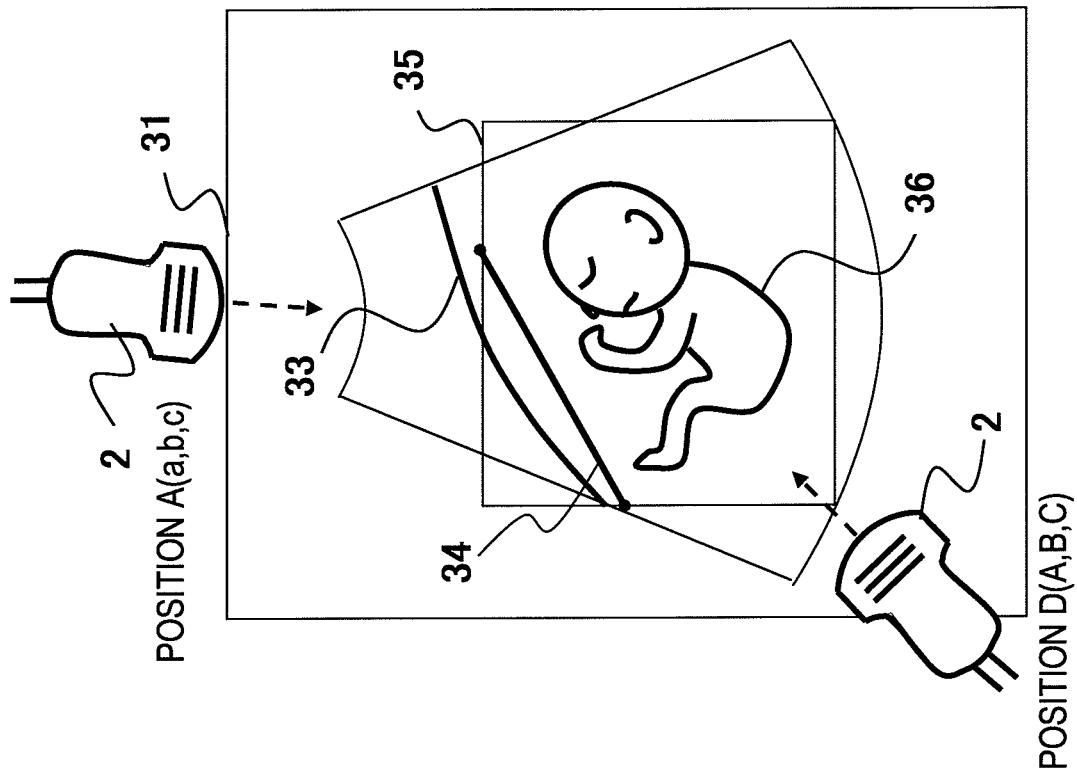

Diagram 31 on the left side of FIG. 7 is related to the pre-cut line setting screen being displayed on display 8. Diagram 32 on the right side is an image diagram related to the 3-dimensional ultrasonic image data processing executed in image processing calculation unit 72 of ultrasonic image construction unit 7. 3-dimensional ultrasonic image data obtained from position A(a,b,c) of ultrasonic probe 2 is the 3-dimensional ultrasonic image data within the range which is specified in set ROI 35. In other words, the ROI 35 has a stereoscopic region. Also, this 3-dimensional ultrasonic image data includes the 3-dimensional ultrasonic image data related to unborn child 36 and the 3-dimensional image data related to placenta 33. Pre-cut line 34 for deleting the 3-dimensional ultrasonic image data related to placenta 33 is set in ROI 35. As shown in pre-cut line setting screen 31, pre-cut line 34 is placed between placenta 33 and unborn child 36. The setting of the pre-cut line 34 is implemented via control panel 10.

When pre-cut line 34 is set, 3-dimensional ultrasonic image data is delimited into two regions having pre-cut line 34 as a borderline. Concretely, in 3-dimensional ultrasonic image data, the region is sterically-delimited in vertical direction with respect to the surface of the 3-dimensional ultrasonic image data, having pre-cut line 34 as an axis. Out of these two delimited regions, one set of 3-dimensional ultrasonic image data is deleted, and the other set of 3-dimensional ultrasonic image data is retained. In the case of the present embodiment, 3-dimensional ultrasonic image region 38 on the side of placenta 33 to which the lateral direction lines are imparted is deleted, and 3-dimensional ultrasonic image region 37 on the side of unborn child 36 is retained. As for the setting of 3-dimensional ultrasonic image region 37, the region is selected manually via control panel 10, the selected region is set as region 37 to be retained, and the other region is set as region 38 to be deleted. Also, image processing calculation unit 72 may be set so that the 3-dimensional ultrasonic image data having less volume will be automatically deleted. Image processing calculating unit 72 reconstructs the 3-dimensional ultrasonic image by a method such as the voxel method or volume rendering method using the 3-dimensional ultrasonic image data in region 37. And the 3-dimensional ultrasonic image thus constructed is displayed in display 8.

Also with respect to the 3-dimensional ultrasonic image data obtained from position D(A,B,C) of ultrasonic probe 2, the position of pre-cut line 34 of position A(a,b,c) of ultrasonic probe 2 is stored in memory 71 in advance, 3-dimensional ultrasonic image data region 38 on the side of placenta 33 colored in gray is deleted, 3-dimensional ultrasonic image data region 38 on the side of unborn child 36 is made to be retained, and image processing calculation unit 72 displays the 3-dimensional ultrasonic image in 3-dimensional ultrasonic image data region 37 on display 8.

In concrete terms, image processing calculation unit 72 in ultrasonic image construction unit 7 causes the position of pre-cut line 34 being set at position A(a,b,c) of ultrasonic probe 2 to be corresponded to the position A(a,b,c) of ultrasonic probe 2, and to be stored in memory 71. It also causes direction of the 3-dimensional ultrasonic image data deleted by pre-cut line 34 to be stored in memory 71. Then it moves ultrasonic probe 2 to position D(A,B,C) and acquires the 3-dimensional ultrasonic image data in position D(A,B,C). With respect to the 3-dimensional ultrasonic image data in position D(A,B,C), the position of pre-cut line 34 being set at position A(a,b,c) and the direction of the 3-dimensional ultrasonic image data being deleted by pre-cut line 34 are read out and made to correspond. More specifically, with respect to the 3-dimensional ultrasonic image data in position D(A,B,C), the position of pre-cut line 34 at position A(a,b,c) of ultrasonic probe 2 is read out and set. Since the position of pre-cut line 34 is stored in memory 71, the 3-dimensional ultrasonic image data region to be deleted is on the side of placenta 33 even when made to correspond to the moving distance and the angle of ultrasonic probe 2.

In this way, the direction for deleting the 3-dimensional ultrasonic image data is set based on pre-cut line 34 set by position D(A,B,C), 3-dimensional ultrasonic image data region 38 on the side of placenta 33 which is colored in gray is deleted, and 3-dimensional ultrasonic image data region 37 on the side of unborn child 36 remains. Then the 3-dimensional ultrasonic image is reconstructed by a method such as a voxel method or volume rendering method using the 3-dimensional ultrasonic image data in region 37 at position D(A,B,C). And the 3-dimensional ultrasonic image in position D(A,B,C) is displayed on display 8.

While the 3-dimensional ultrasonic image being scanned at position A(a,b,c) of ultrasonic probe 2 transmits/receives ultrasonic waves via obstacles such as placenta 33, there are no obstacles such as placenta 33 in the path of transmitting/receiving ultrasonic waves to/from position D (A,B,C) that is between ultrasonic probe 2 and the unborn child. In other words, in accordance with embodiment 5, a clearer 3-dimensional ultrasonic image can be displayed when imaged from position D (A,B,C) of ultrasonic probe 2 rather than being imaged from position A(a,b,c), since there are no obstacles such as placenta 33 upon transmitting/receiving ultrasonic waves.

In addition, the above-described embodiments 1~5 can be combined to be executed, and an operator can arbitrarily select any embodiments to be combined. Also, ultrasonic image construction unit 7 may construct blood flow images from Doppler signals that are a kind of ultrasonic receiving signals. Then the 3-dimensional ultrasonic image and the 3-dimensional image of the blood flow image may be separately reconstructed, and a B-mode image and the blood flow image may be synthesized or displayed in parallel on the 3-dimensional image.

The invention claimed is:

1. An ultrasonic diagnostic apparatus comprising:
   an ultrasonic probe for configured to transmit/receive ultrasonic waves to/from an object to be examined at a first display position and a second display position, including a position sensor configured to detect the first display position and the second display position of the ultrasonic probe;
   an ultrasonic image construction unit configured to construct a 3-dimensional ultrasonic image from 3-dimensional ultrasonic image data, which is obtained from the ultrasonic signals received from the ultrasonic probe;
   a display unit configured to display the 3-dimensional ultrasonic image constructed by the ultrasonic image construction unit; and
   a positional information analysis unit configured to store a first display position of the ultrasonic probe acquired from the position sensor and to analyze a positional relationship between the stored first display position and the second display position of the ultrasonic probe,
   wherein the first display position and the second display position are different from each other, and the ultrasonic image construction unit configured to convert 3-dimensional ultrasonic image data acquired at the second display position into the view point of the three-dimensional ultrasonic data acquired at the first position based on the positional relationship,
   wherein the ultrasonic image construction unit comprises memory configured to store the 3-dimensional ultrasonic images acquired at the first position and to cause the stored 3-dimensional ultrasonic images and a 3-dimensional ultrasonic image at the second position to be synthesized, and
   wherein the ultrasonic image construction unit is configured to cause a 3-dimensional ultrasonic image having the higher luminance, out of the stored 3-dimensional ultrasonic image at the first display position and the 3-dimensional ultrasonic image at the second display position, to be displayed.

2. The ultrasonic diagnostic apparatus according to claim 1, wherein the positional information analyzing unit configured to analyze the positional relationship based on variation between the first display position and the second display position and variation of a 3-dimensional rotation angle of the ultrasonic probe.

3. The ultrasonic diagnostic apparatus according to claim 1, wherein the positional information analyzing unit is configured to compute an adjustment parameter for converting the 3-dimensional ultrasonic image data from conversion information indicating the first display position of the ultrasonic probe and conversion information indicating the second display position of the ultrasonic probe.

4. The ultrasonic diagnostic apparatus according to claim 1, wherein the second display position is displayed on the display unit as in indicator mark, and the ultrasonic image construction unit is configured to convert the 3-dimensional ultrasonic image data in the second display position into a viewpoint of the 3-dimensional ultrasonic image data acquired in the position specified by the indicator mark, and to construct a 3-dimensional ultrasonic image in the display position of the indicator mark.

5. The ultrasonic diagnostic apparatus according to claim 4, wherein the display unit the indicator mark 3-dimensionally along with the 3-dimensional ultrasonic image.

6. The ultrasonic diagnostic apparatus according to claim 1, wherein the ultrasonic image construction unit a line for indicating a sliced plane of a B-mode image corresponding to the 3-dimensional ultrasonic image to be displayed on the 3-dimensional ultrasonic image, and the B-mode image corresponding to the line.

7. The ultrasonic diagnostic apparatus according to claim 1, wherein the ultrasonic image construction unit reference coordinates of the 3-dimensional ultrasonic image data at the first display position and the 3-dimensional ultrasonic image data at the second display position.

8. The ultrasonic diagnostic apparatus according to claim 1, wherein the ultrasonic image construction unit configured to cause the 3-dimensional ultrasonic image data at the first display position to be partially deleted, and constructs the 3-dimensional ultrasonic image.

9. The ultrasonic diagnostic apparatus according to claim 8 comprising an operation unit configured to set a pre-cut line for partially deleting the 3-dimensional ultrasonic image data at the first display position, wherein the ultrasonic image construction unit configured to delete one part of the 3-dimensional ultrasonic image data being delimited by the pre-cut line and to construct a 3-dimensional ultrasonic image from the remaining data.

10. The ultrasonic diagnostic apparatus according to claim 9, wherein:
    the display unit is configured to display the 3-dimensional ultrasonic image; and
    the operation unit configured to set the pre-cut line with respect to the 3-dimensional ultrasonic image.

11. The ultrasonic diagnostic apparatus according to claim 1, wherein the first display position is a position for scanning a frontal image of the object, and the second display position is a position for scanning a lateral image of the object.

12. The ultrasonic diagnostic apparatus according to claim 1, wherein the positional information analyzing unit configured to set the first display position of the ultrasonic probe as a first conversion matrix, to be the display position of the 3-dimensional ultrasonic image, to set the second display position as the second conversion matrix, and to compute an adjustment parameter of the 3-dimensional ultrasonic image data at the second display position.

13. The ultrasonic diagnostic apparatus according to claim 12, wherein the ultrasonic image construction unit is configured to perform a coordinate conversion of the 3-dimensional ultrasonic image based on the adjustment parameter, and changes a display direction of the 3-dimensional ultrasonic image.

14. The ultrasonic diagnostic apparatus according to claim 1, wherein:
- the positional information analyzing unit is configured to compute variation of the second display position with respect to the first display position and displacement magnitude of the 3-dimensional rotation angle thereof; and
- the image processing calculation unit is configured to rotate the 3-dimensional ultrasonic image for the variation of the position and the angle.

15. An ultrasonic imaging method comprising:
- a step to set an ultrasonic probe at a first display position;
- a step to detect the first display position by a position sensor which is included in the ultrasonic probe;
- a step to transmit/receive ultrasonic waves to/from an object to be examined at the first display position by the ultrasonic probe;
- a step to construct a 3-dimensional ultrasonic image from 3-dimensional ultrasonic image data which is obtained from the ultrasonic signals received from the ultrasonic probe at the first display position by an ultrasonic image construction unit;
- a step to display a step to store the 3-dimensional ultrasonic image; the 3-dimensional ultrasonic image by a display unit;
- a step to store the first display position in a positional information analysis unit;
- a step to set the ultrasonic probe at a second display position different from the first display position;
- a step to detect the second display position by the position sensor;
- a step to transmit/receive ultrasonic waves to/from an object to be examined at a second display position by the ultrasonic probe;
- a step to acquire 3-dimensional ultrasonic image data based on the ultrasonic signals received from the ultrasonic probe at the second display position by the ultrasonic image construction unit;
- a step to analyze a positional relationship between storing the first display position and a second display position of the ultrasonic probe by the positional information analysis unit;
    - a step to convert 3-dimensional ultrasonic image data acquired at the second display position into a viewpoint of the 3-dimensional ultrasonic image data acquired at the first display position based on a positional relationship by the ultrasonic image construction unit,
- a step to construct a converted 3-dimensional image based on the converted 3-dimensional ultrasonic image data acquired at the second display position;
- a step to display the 3-dimensional ultrasonic image having the higher luminance, out of the stored 3-dimensional ultrasonic image at the first display position and the converted 3-dimensional ultrasonic image at the second display position.

* * * * *